(12) United States Patent
Ho et al.

(10) Patent No.: US 11,999,944 B2
(45) Date of Patent: Jun. 4, 2024

(54) METHOD FOR PROMOTING GROWTH OF PROBIOTIC MICROORGANISM

(71) Applicant: GLAC BIOTECH CO., LTD., Tainan (TW)

(72) Inventors: Hsieh-Hsun Ho, Tainan (TW); Ching-Wei Chen, Tainan (TW); Yu-Fen Huang, Tainan (TW); Cheng-Chi Lin, Tainan (TW); Chen-Hung Hsu, Tainan (TW); Tsai-Hsuan Yi, Tainan (TW); Yu-Wen Chu, Tainan (TW); Yi-Wei Kuo, Tainan (TW); Jui-Fen Chen, Tainan (TW); Shin-Yu Tsai, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

(21) Appl. No.: 17/724,341

(22) Filed: Apr. 19, 2022

(65) Prior Publication Data
US 2023/0100778 A1     Mar. 30, 2023

(30) Foreign Application Priority Data
Sep. 24, 2021    (TW) ................................ 110135628

(51) Int. Cl.
| | |
|---|---|
| *C12N 1/20* | (2006.01) |
| *C12N 1/36* | (2006.01) |
| *C12R 1/23* | (2006.01) |
| *C12R 1/25* | (2006.01) |

(52) U.S. Cl.
CPC ............... *C12N 1/205* (2021.05); *C12N 1/36* (2013.01); *C12R 2001/23* (2021.05); *C12R 2001/25* (2021.05)

(58) Field of Classification Search
CPC ...... C12N 1/205; C12N 1/36; C12R 2001/23; C12R 2001/25
See application file for complete search history.

(56) References Cited

PUBLICATIONS

Lin et al. (The Function of Mixed Postbiotic PE0401 in Improving Intestinal Health via Elevating Anti-inflammation, Anti-oxidation, Epithelial Tight Junction Gene Expression and Promoting Beneficial Bacteria Growth. J Pure Appl Microbiol. Jul. 25, 2022. doi: 10.22207/JPAM.16.3.19) (Year: 2022).*

Ho et al. (The Postbiotics, Totipro PE0401, and Probiotic Mixture, PF1001, Modulate the Gut Microbiota and Ameliorate Diarrhea in Weaning Piglets, Biomed J Sci & Tech Res, vol. 28 Issue 1, May 29, 2020) (Year: 2020).*

Raminta Pranckute, et al., "Combining prebiotics with probiotic bacteria can enhance bacterial growth and secretion of bacteriocins" International Journal of Biological Macromolecules, 89, p. 669-676 (2016).

* cited by examiner

*Primary Examiner* — Robert J Yamasaki
*Assistant Examiner* — Alexander M Duryee
(74) *Attorney, Agent, or Firm* — HSML P.C.

(57) ABSTRACT

A method for promoting growth of a probiotic microorganism includes cultivating the probiotic microorganism in a growth medium containing a fermented culture of lactic acid bacterial strains that include *Lactobacillus salivarius* subsp. *salicinius* AP-32 deposited at the China Center for Type Culture Collection (CCTCC) under CCTCC M 2011127, *Lactobacillus plantarum* LPL28 deposited at the China General Microbiological Culture Collection Center (CGMCC) under CGMCC 17954, *Lactobacillus acidophilus* TYCA06 deposited at the CGMCC under CGMCC 15210, and *Bifidobacterium longum* subsp. *infantis* BLI-02 deposited at the CGMCC under CGMCC 15212.

5 Claims, 4 Drawing Sheets

METHOD FOR PROMOTING GROWTH OF PROBIOTIC MICROORGANISM

CROSS-REFERENCE TO RELATED APPLICATION

This application claims priority of Taiwanese Invention Patent Application No. 110135628, filed on Sep. 24, 2021.

FIELD

The present disclosure relates to a method for promoting growth of a probiotic microorganism.

BACKGROUND

Probiotic microorganisms are a type of live microbial food ingredient which is beneficial to health, and may selectively stimulate the growth of native bacteria in the intestinal tract. Probiotic microorganisms have been reported to exert effects such as inhibiting the growth of pathogens in the gastrointestinal tract, alleviating lactose intolerance, improving immunoregulatory function, providing anti-cancer properties, lowering blood pressure, etc. Examples of common probiotic microorganisms include *Lactobacillus* spp., *Bifidobacterium* spp., *Bacillus* spp., *Lactococcus* spp., *Enterococcus* spp., *Saccharomyces* spp., *Streptococcus* spp., etc.

Prebiotics are oligosaccharides or polysaccharides which cannot be digested by the human body, and may selectively promote the activity and growth of bacteria in the intestinal tract, particularly probiotic microorganisms. Examples of common prebiotics include fructooligosaccharides, inulin, xylooligosaccharides, pectic oligosaccharides, palatinose, etc.

Previous studies have demonstrated that certain types of prebiotics might exert growth-promoting effects only on certain types of probiotic microorganisms. For example, as reported by Pranckutė R. et al. (2016), *Int. J. Biol. Macromol.*, 89:669-676, when inulin and palatinose are used for culturing *Lactobacillus casei* A11, *Lactobacillus paracasei* B13, *Lactobacillus lactis* subsp. *lactis* DSM 20729 and *Lactobacillus acidophilus* DSM 20079, inulin can only promote the growth of *Lactobacillus paracasei* B13, while palatinose cannot promote the growth of all the aforesaid probiotic microorganisms.

Therefore, there is still a need to develop a new strategy that can be utilized for effectively promoting the growth of various types of probiotic microorganisms.

SUMMARY

The present disclosure provides a method for promoting growth of a probiotic microorganism, which can alleviate at least one of the drawbacks of the prior art, and which includes cultivating the probiotic microorganism in a growth medium containing a fermented culture of lactic acid bacterial strains.

The lactic acid bacterial strains include *Lactobacillus salivarius* subsp. *salicinius* AP-32 which is deposited at the China Center for Type Culture Collection (CCTCC) under an accession number CCTCC M 2011127, *Lactobacillus plantarum* LPL28 which is deposited at the China General Microbiological Culture Collection Center (CGMCC) under an accession number CGMCC 17954, *Lactobacillus acidophilus* TYCA06 which is deposited at the CGMCC under an accession number CGMCC 15210, and *Bifidobacterium longum* subsp. *infantis* BLI-02 which is deposited at the CGMCC under an accession number CGMCC 15212.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In the development of methods for promoting growth of probiotic microorganisms, the applicant surprisingly found that, contrary to conventional teachings of using prebiotics, certain lactic acid bacterial strains, when used in combination, are capable of greatly promoting growth of various types of probiotic microorganisms, and hence are expected to be effective in promoting growth of probiotic microorganisms.

Therefore, the present disclosure provides a method for promoting growth of a probiotic microorganism, which includes cultivating the probiotic microorganism in a growth medium containing a fermented culture of lactic acid bacterial strains.

The lactic acid bacterial strains include *Lactobacillus salivarius* subsp. *salicinius* AP-32 which is deposited at the China Center for Type Culture Collection (CCTCC) under an accession number CCTCC M 2011127, *Lactobacillus*

*plantarum* LPL28 which is deposited at the China General Microbiological Culture Collection Center (CGMCC) under an accession number CGMCC 17954, *Lactobacillus acidophilus* TYCA06 which is deposited at the CGMCC under an accession number CGMCC 15210, and *Bifidobacterium longum* subsp. *infantis* BLI-02 which is deposited at the CGMCC under an accession number CGMCC 15212.

According to the present disclosure, the growth medium for cultivating the probiotic microorganism may be prepared by adding the fermented culture of the lactic acid bacterial strains to a basal medium suitable for growing the probiotic microorganism. In certain embodiments, the fermented culture of the lactic acid bacterial strains may be added to the basal medium in an amount ranging from 0.1 wt % to 10 wt % based on the total weight of the growth medium. In other embodiments, the fermented culture of the lactic acid bacterial strains may be added to the basal medium in an amount ranging from 0.25 wt % to 0.5 wt % based on the total weight of the growth medium. In an exemplary embodiment, the fermented culture of the lactic acid bacterial strains may be added to the basal medium in an amount of 0.25 wt % based on the total weight of the growth medium. In another exemplary embodiment, the fermented culture of the lactic acid bacterial strains may be added to the basal medium in an amount of 0.5 wt % based on the total weight of the growth medium.

According to the present disclosure, the basal medium may be purchased commercially or self-prepared using standard techniques well known to those skilled in the art. Examples of the basal medium that are purchased commercially may include, but are not limited to, MRS (De Man, Rogosa and Sharpe) broth and MRS broth supplemented with cysteine.

According to the present disclosure, the basal medium may include a carbon source selected from the group consisting of glucose, fructose, lactose, sucrose, maltose, galactose, mannose, trehalose, starch, potato starch, malt extract, maltodextrin, and combinations thereof. In certain embodiments, the basal medium may include 1 wt % to 5 wt % of glucose based on the total weight of the basal medium. In an exemplary embodiment, the basal medium may include 5 wt % of glucose based on the total weight of the basal medium.

According to the present disclosure, the basal medium may include a nitrogen source selected from the group consisting of ammonium sulfate [$(NH_4)_2SO_4$], ammonium phosphate [$(NH_4)_3PO_4$], ammonium nitrate ($NH_4NO_3$), ammonium chloride ($NH_4Cl$), casamino acid, peptone, polypeptone, tryptone, meat extract, yeast extract, yeast powder, milk, skimmed milk powder, soybean flour, whey, and combinations thereof. In certain embodiments, the basal medium may include, based on the total weight of the basal medium, 2 wt % to 15 wt % of skimmed milk powder, 3 wt % to 10 wt % of peptone, and 1 wt % to 5 wt % of yeast extract. In an exemplary embodiment, the basal medium includes, based on the total weight of the basal medium, 12 wt % of skimmed milk powder, 7 wt % of peptone, and 3% wt % of yeast extract.

As used herein, the term "cultivating" can be used interchangeably with other terms such as "fermentation" and "culturing".

It should be noted that the procedures and operating conditions for cultivating the probiotic microorganism may be adjusted according to practical requirements. In this regard, those skilled in the art may refer to journal articles, e.g., Hsieh P. S. et al. (2013), *New Microbiol.*, 36:167-179.

According to the present disclosure, the cultivation of the probiotic microorganism may be performed at a temperature ranging from 25° C. to 40° C. In an exemplary embodiment, the cultivation of the probiotic microorganism is performed at a temperature of 37° C.

According to the present disclosure, the cultivation of the probiotic microorganism may be performed for a time period ranging from 6 hours to 12 hours. In an exemplary embodiment, the cultivation of the probiotic microorganism is performed for a time period of 6 hours.

According to the present disclosure, the fermented culture of the lactic acid bacterial strains is obtained by cultivating *Lactobacillus salivarius* subsp. *salicinius* AP-32, *Lactobacillus plantarum* LPL28, *Lactobacillus acidophilus* TYCA06, and *Bifidobacterium longum* subsp. *infantis* BLI-02 in a number ratio ranging from 1:0.2:0.2:0.2 to 1:5:5:5 in a liquid medium (i.e., the aforesaid basal medium) suitable for growth thereof. In an exemplary embodiment, the fermented culture of the lactic acid bacterial strains is obtained by cultivating *Lactobacillus salivarius* subsp. *salicinius* AP-32, *Lactobacillus plantarum* LPL28, *Lactobacillus acidophilus* TYCA06, and *Bifidobacterium longum* subsp. *infantis* BLI-02 in a number ratio of 1:1:1:1.

According to the present disclosure, the lactic acid bacterial strains may be cultivated using procedures and operating conditions which are similar to those described above for cultivating the probiotic microorganism.

According to the present disclosure, the fermented culture may be prepared by conducting a solid-liquid separation treatment after the cultivation of the lactic acid bacterial strains, and is substantially free of bacterial cells.

As used herein, the term "substantially free of" means that the fermented culture lacks a significant amount of a specified component (i.e., bacterial cells). In certain embodiments, the amount of the bacterial cells does not have a measurable effect on the properties of the fermented culture. In other embodiments, the fermented culture is completely free of bacterial cells.

According to the present disclosure, the solid-liquid separation treatment may be selected from the group consisting of a centrifugation treatment, a filtration treatment, a concentration treatment, and combinations thereof. In an exemplary embodiment, the solid-liquid separation treatment is a centrifugation treatment.

According to the present disclosure, the fermented culture may be prepared by conducting a drying treatment using techniques well-known to those skilled in the art after the solid-liquid separation treatment. Examples of the drying treatment may include, but are not limited to, a freeze-drying treatment, a spray-drying treatment, a fluidized bed-drying treatment, and combinations thereof.

As used herein, the terms "probiotic" and "probiotic microbe" are used interchangeably, and refer to preparations of live microorganisms. These microorganisms may remain and survive in the gastrointestinal tract after ingestion by a subject, and can exert a desired effect (e.g., adjusting the gut microbiota, providing a preventive or therapeutic effect, etc.).

According to the present disclosure, the probiotic microorganism may be selected from the group consisting of *Lactobacillus* spp., *Lactococcus* spp., *Pediococcus* spp., *Enterococcus* spp., *Streptococcus* spp., *Bifidobacterium* spp., *Bacillus* spp., *Leuconostoc* spp., and combinations thereof.

In certain embodiments, the *Lactobacillus* spp. may be selected from the group consisting of *Lactobacillus gasseri, Lactobacillus fermentum, Lactobacillus johnsonii, Lactobacillus reuteri, Lactobacillus helveticus, Lactobacillus casei, Lactobacillus paracasei, Lactobacillus rhamnosus, Lactobacillus delbrueckii, Lactobacillus bulgaricus, Lactobacillus salivarius, Lactobacillus plantarum, Lactobacillus acidophilus,* and combinations thereof. In an exemplary embodiment, the *Lactobacillus* spp. is selected from the group consisting of *Lactobacillus gasseri* AI-88, *Lactobacillus gasseri* LG21, *Lactobacillus fermentum* CECT5716, *Lactobacillus johnsonii* MH-68, *Lactobacillus reuteri* GL-104, *Lactobacillus helveticus* RE-78, *Lactobacillus paracasei* MP137, *Lactobacillus paracasei* ET-66, *Lactobacillus rhamnosus* MP108, *Lactobacillus rhamnosus* CT-53, *Lactobacillus rhamnosus* LGG, *Lactobacillus plantarum* LPL28, *Lactobacillus plantarum* TSP05, *Lactobacillus acidophilus* TCYA06, and *Lactobacillus acidophilus* LA-5.

In certain embodiments, the *Lactococcus* spp. may be *Lactococcus lactis,* e.g., *Lactococcus lactis* subsp. *lactis*. In an exemplary embodiment, the *Lactococcus* spp. is *Lactococcus lactis* subsp. *lactis* LY-66.

In certain embodiments, the *Streptococcus* spp. may be *Streptococcus thermophilus.* In an exemplary embodiment, the *Streptococcus* spp. is selected from *Streptococcus thermophilus* SY-66 and *Streptococcus thermophilus* UASt-09.

In certain embodiments, the *Bifidobacterium* spp. may be selected from the group consisting of *Bifidobacterium animalis* (e.g., *Bifidobacterium animalis* subsp. *lactis* and *Bifidobacterium animalis* subsp. *lactis* Bb), *Bifidobacterium breve, Bifidobacterium longum* (e.g., *Bifidobacterium longum* subsp. *infantis*), *Bifidobacterium bidifium, Bifidobacterium adolescentis, Bifidobacterium infantis,* and combinations thereof. In an exemplary embodiment, the *Bifidobacterium* spp. is selected from the group consisting of *Bifidobacterium animalis* subsp. *lactis* CP-9, *Bifidobacterium animalis* subsp. *lactis* BB-12, *Bifidobacterium animalis* subsp. *lactis* Bb BB-115, *Bifidobacterium longum* subsp. *infantis* BLI-02, *Bifidobacterium breve* Bv-889, and *Bifidobacterium longum* BB536.

In certain embodiments, the probiotic microorganism includes a combination of *Lactobacillus* spp. and *Bifidobacterium* spp., for example, a combination of *Lactobacillus rhamnosus, Bifidobacterium animalis,* and *Bifidobacterium longum.* In an exemplary embodiment, the probiotic microorganism includes a combination of *Lactobacillus rhamnosus* MP108, *Bifidobacterium animalis* subsp. *lactis* Bb BB-115, and *Bifidobacterium longum* subsp. *infantis* BLI-02.

The present disclosure also provides a method for enriching probiotic microorganisms, which includes cultivating the aforesaid probiotic microorganisms in a growth medium containing a fermented culture of the aforesaid lactic acid bacterial strains. The growth medium and the fermented culture of the lactic acid bacterial strains are prepared using procedures and conditions as mentioned in the foregoing.

The present disclosure will be further described by way of the following examples. However, it should be understood that the following examples are intended solely for the purpose of illustration and should not be construed as limiting the present disclosure in practice.

EXAMPLES

General Experimental Materials:
1. Growth Medium

The growth medium used in the following examples was prepared using the recipe shown in Table 1 below.

TABLE 1

| Ingredients | Source | Amount (wt %) |
|---|---|---|
| Glucose | Union Chemical Co., Ltd. | 1-5 |
| Skimmed milk powder | Warrnambool Cheese & Butter Factory Company Holdings Ltd. | 2-15 |
| Peptone | STBIO MEDIA, Inc. | 3-10 |
| Yeast extract | Angel Yeast Co., Ltd. | 1-5 |
| Potassium hydrogen phosphate | Budenheim USA, Inc. | 0.05-0.2 |
| Sodium citrate | Qingdao Fuso Refining & Processing Co., Ltd. | 0-0.01 |
| Manganese (II) sulfate ($MnSO_4$) | Jost Chemical Co. | 0-0.01 |
| Monosodium glutamate (MSG) | PT Cheil Jedang Indonesia | 1-5 |
| Tween 80 | Musim Mas Holdings | 0.05-0.2 |

The balance is deionized water.

2. Lactic Acid Bacterial (LAB) Strains
A. *Lactobacillus Salivarius* subsp. *Salicinius* AP-32

*Lactobacillus salivarius* subsp. *salicinius* AP-32, which is disclosed in the applicant's patent TN 1709374 B and is known and readily available to the public, has been deposited at the Bioresource Collection and Research Center (BCRC) of the Food Industry Research and Development Institute (FIRDI) (No. 331, Shih-Pin Rd., Hsinchu City 300, Taiwan) under an accession number BCRC 910437 since Jul. 30, 2009, and has also been deposited at the China Center for Type Culture Collection (CCTCC) of Wuhan University, the College of Life Sciences (No. 299, Bayi Rd., Wuchang District, Wuhan City 430072, Hubei Province, China) under an accession number CCTCC 2011127 since Apr. 10, 2011 according to the Budapest Treaty.

B. *Lactobacillus Plantarum* LPL28

*Lactobacillus plantarum* LPL28, which is disclosed in the applicant's patent TW 1739495 B and is known and readily available to the public, has been deposited at the BCRC of the FIRDI under an accession number BCRC 910536 since Dec. 27, 2011, and has also been deposited at the China General Microbiological Culture Collection Center (CGMCC) of Chinese Academy of Sciences, the institute of Microbiology (No. 1, West Beichen Rd., Chaoyang District, Beijing 100101, China) under an accession number CGMCC 17954 since Jun. 18, 2019 according to the Budapest Treaty.

C. *Lactobacillus Acidophilus* TYCA06

*Lactobacillus acidophilus* TYCA06, which is disclosed in TW 1709374 B and is known and readily available to the public, has been deposited at the BCRC of the FIRDI under an accession number BCRC 910813 since Jan. 18, 2018, and has also been deposited at the CGMCC of Chinese Academy of Sciences, the Institute of Microbiology, under an accession number CGMCC 15210 since Jan. 15, 2018 according to the Budapest Treaty.

D. *Bifidobacterium Longum* subsp. *Infantis* BLI-02 *Bifidobacterium longum* subsp. *infantis* BLI-02, which is disclosed in TW 1739495 B and is known and readily available to the public, has been deposited at the BCRC of the FIRDI under an accession number BCRC 910812 since Jan. 18, 2018, and has also been deposited at the CGMCC of Chinese Academy of Sciences, the Institute of Microbiology, under an accession number CGMCC 15212 since Jan. 15, 2018 according to the Budapest Treaty.

3. Prebiotics

The prebiotics used in the following examples and source thereof are listed in Table 2 below.

TABLE 2

| Prebiotics | Source |
|---|---|
| Human milk oligosaccharides | DuPont Co. |
| Maltodextrin | Union Food Co., Ltd. |
| Fructooligosaccharides | Greengo Biomedical International Co., Ltd. |
| Galactooligosaccharides | |
| Sorbitol | Sheng Yuang Food Industrial Co., Ltd. |
| Erythritol | Buildmore Enterprise Co., Ltd. |
| Inulin | Biomed Herbal Research Co., Ltd. |

4. Probiotic Microorganisms

The probiotic microorganisms used in the following examples and relevant information thereof (including the genus and strains, BCRC accession number and corresponding CGMCC or CCTCC accession number (if any), and source) are listed in Table 3 below.

TABLE 3

| Genus | Strain | Accession number | Source |
|---|---|---|---|
| Lactobacillus | Lactobacillus gasseri AI-88 | BCRC 910943; CGMCC 18693 | Isolated from breast milk by the applicant |
| | Lactobacillus gasseri LG21 | — | Purchased from Meiji Co., Ltd., Japan |
| | Lactobacillus fementum CECT5716 | — | Purchased from Biosearch Life Camino de Purchil, Spain |
| | Lactobacillus johnsonii MH-68 | BCRC 910438 | Isolated from feces of a healthy subject by the applicant |
| | Lactobacillus reuteri GL-104 | BCRC 910404; CCTCC M 209138 | |
| | Lactobacillus helveticus RE-78 | BCRC 910537; CGMCC 13513 | Isolated from a fermented vegetable by the applicant |
| | Lactobacillus paracasei MP137 | BCRC 910484; CGMCC 21224 | Isolated from feces of a healthy infant subject by the applicant |
| | Lactobacillus paracasei ET-66 | BCRC 910753; CGMCC 13514 | Isolated from breast milk by the applicant |
| | Lactobacillus rhamnosus MP108 | BCRC 910483; CGMCC 21225 | Isolated from feces of a healthy infant subject by the applicant |
| | Lactobacillus rhamnosus CT-53 | BCRC 910468; CCTCC 2011129 | Isolated from vaginal discharge of a healthy subject by the applicant |
| | Lactobacillus rhamnosus LGG | — | Purchased from Chr. Hansen A/S, Denmark |
| | Lactobacillus plantarum LPL28 | BCRC 910536; CGMCC 17954 | Isolated from miso by the applicant |

TABLE 3-continued

| Genus | Strain | Accession number | Source |
|---|---|---|---|
| | Lactobacillus plantarum TSP05 | BCRC 910855; CGMCC 16710 | Isolated from a fermented vegetable by the applicant |
| | Lactobacillus acidophilus TYCA06 | BCRC 910813; CGMCC 15210 | Isolated from feces of a healthy infant subject by the applicant |
| | Lactobacillus acidophilus LA-5 | — | Purchased from Chr. Hansen A/S, Denmark |
| Lactococcus | Lactococcus lactis subsp. lactis LY-66 | BCRC 911055; CGMCC 21838 | Isolated from feces of a healthy subject by the applicant |
| Streptococcus | Streptococcus thermophilus SY-66 | BCRC 911043; CGMCC 21839 | Isolated from a fermented dairy product by the applicant |
| | Streptococcus thermophilus UASt-09 | — | Purchased from Chr. Hansen A/S, Denmark |
| Bifidobacterium | Bifidobacterium animalis subsp. lactis CP-9 | BCRC 910645; CCTCC M 2014588 | Isolated from breast milk by the applicant |
| | Bifidobacterium animalis subsp. lactis BB-12 | — | Purchased from Chr. Hansen A/S, Denmark |
| | Bifidobacterium animalis subsp. lactis Bb BB-115 | BCRC 911045; CGMCC 21840 | Isolated from feces of a healthy subject by the applicant |
| | Bifidobacterium longum subsp. infantis BLI-02 | BCRC 910812; CGMCC 15212 | Isolated from breast milk by the applicant |
| | Bifidobacterium breve Bv-889 | BCRC 910844; CGMCC 16145 | |
| | Bifidobacterium longum BB536 | — | Purchased from Morinaga & Co., Ltd., Japan |

General Procedures:

1. Preparation of Bacterial Cultures of Probiotic Strains

First, a respective one of the probiotic strains described in section 4 of the General Experimental Materials was activated by inoculating into 5 mL of a Difco™ Lactobacilli MRS (De Man, Rogosa and Sharpe) broth (Manufacturer: BD; Catalogue no.: DF0881-17-5) supplemented with 0.05% (w/w) cysteine, and was then cultured at 37° C. and 5% $CO_2$ for 16 hours to obtain a probiotic inoculum. Next, the probiotic inoculum was inoculated in an amount of 10% (v/v) into a Difco™ Lactobacilli MRS broth, and was then sub-cultured in an incubator (37° C., 5% $CO_2$) for 24 hours, thereby obtaining a bacterial culture having a bacterial concentration that was adjusted to $1\times10^9$ CFU/mL using a Difco™ Lactobacilli MRS broth.

In addition, a probiotic mixture was prepared by mixing a portion of each of the bacterial cultures of *Lactobacillus rhamnosus* MP108, *Bifidobacterium animalis* subsp. *lactis* Bb BB-115, and *Bifidobacterium longum* subsp. *infantis* BLI-02 in a volume ratio of 1:1:1.

2. Statistical Analysis

All the experiments described below were performed in triplicates. The experimental data of all the test groups are expressed as mean±standard error of the mean (SEM), and were analyzed using two-tailed Student's t-test using Graph-Pad Prism 5 software (Developer: GraphPad Software, Inc., San Diego, Calif.), so as to assess the differences between the groups. Statistical significance is indicated by $p<0.05$.

Example 1. Preparation of LAB Fermented Culture Supernatant

First, a respective one of the four LAB strains described in section 2 of the General Experimental Materials was inoculated into 100 mL of a growth medium (as described in section 1 of the General Experimental Material), and was then cultured at 37° C. for 24 hours to obtain an activated LAB inoculum having a bacterial concentration of $1\times10^9$ CFU/mL. Next, the LAB inoculum was inoculated in an amount of 3% (v/v) into 5 L of a growth medium (as described in section 1 of the General Experimental Material), and was then cultured under a condition suitable for fermentation (i.e., 37° C., anaerobic, and overnight) to obtain a single-LAB fermented culture, i.e., a corresponding one of single-LAB fermented cultures 1 to 4 as shown in Table 4.

In addition, the activated LAB inoculums of *Lactobacillus salivarius* subsp. *salicinius* AP-32, *Lactobacillus plantarum* LPL28, *Lactobacillus acidophilus* TYCA06, and *Bifidobacterium longum* subsp. *infantis* BLI-02 were mixed at a specified number ratio shown in Table 5. The resultant LAB inoculum mixture was cultivated using the aforesaid procedures and conditions, thereby obtaining a four-LAB fermented culture, i.e., a corresponding one of four-LAB fermented cultures 1 to 5 as shown in Table 5.

TABLE 4

| LAB fermented culture | LAB strain |
|---|---|
| Single-LAB fermented culture 1 | *Lactobacillus salivarius* subsp. *salicinius* AP-32 |
| Single-LAB fermented culture 2 | *Lactobacillus plantarum* LPL28 |
| Single-LAB fermented culture 3 | *Lactobacillus acidophilus* TYCA06 |
| Single-LAB fermented culture 4 | *Bifidobacterium longum* subsp. *infantis* BLI-02 |

TABLE 5

| LAB fermented culture | Ratio of number of *Lactobacillus salivarius* subsp. *salicinius* AP-32, *Lactobacillus plantarum* LPL28, *Lactobacillus acidophilus* TYCA06, and *Bifidobacterium longum* subsp. *infantis* BLI-02 |
|---|---|
| Four-LAB fermented culture 1 | 1:0.2:0.2:0.2 |
| Four-LAB fermented culture 2 | 1:1:1:1 |
| Four-LAB fermented culture 3 | 1:5:1:1 |
| Four-LAB fermented culture 4 | 1:1:5:1 |
| Four-LAB fermented culture 5 | 1:1:1:5 |

The respective fermented culture shown in Tables 4 and 5 was subjected to centrifugation at 25° C. under a speed of 12,000×g for 10 minutes to form a LAB fermented culture supernatant and a pellet. Subsequently, the LAB fermented culture supernatant was collected, and was then subjected to a heat-sterilization treatment, followed by a spray-drying treatment so as to obtain a spray-dried powder of LAB fermented culture supernatant. Thereafter, the spray-dried powder of LAB fermented culture supernatant was dissolved in 4.5 mL of a growth medium as described in section 1 of the General Experimental Material, in an amount of 0.5 wt % based on the total weight of the growth medium. The resultant growth medium containing a respective one of different single-LAB fermented culture supernatants (i.e., the single-LAB fermented culture supernatants 1 to 4) or four-LAB fermented culture supernatants (i.e., the four-LAB fermented culture supernatants 1 to 5) was used in the following experiments.

Example 2. Evaluation of the Effect of LAB Fermented Culture Supernatant on Promotion of Growth of a Probiotic Strain In order to evaluate the efficacy of the LAB fermented culture supernatant according to the present disclosure on growth promotion of *Lactobacillus rhamnosus* MP108, the following experiments were conducted.

Experimental Procedures:

The bacterial culture of *Lactobacillus rhamnosus* MP108 obtained in section 1 of the General Procedures was divided into 9 groups, namely, a control group, four comparative groups (i.e., comparative groups 1 to 4), and five experimental groups (i.e., experimental groups 1 to 5), each having a volume of 5 μL. Next, as shown in Table 6 below, the bacterial cultures of *Lactobacillus rhamnosus* MP108 of the experimental groups 1 to 5 and comparative groups 1 to 4 were respectively inoculated into the growth mediums containing different LAB fermented culture supernatants prepared in Example 1, while the bacterial culture of *Lactobacillus rhamnosus* MP108 of the control group was inoculated into a growth medium not containing any of the aforesaid LAB fermented culture supernatant. In addition, a growth medium (i.e., an MRS broth) free of any of the probiotic strain and any of the LAB fermented culture supernatant served as a blank control group. Then, each group was subjected to cultivation at 37° C. for 6 hours, thereby obtaining a liquid culture of *Lactobacillus rhamnosus* MP108.

TABLE 6

| Group | LAB fermented culture supernatant |
|---|---|
| Control group | — |
| Comparative group 1 | Single-LAB fermented culture supernatant 1 |
| Comparative group 2 | Single-LAB fermented culture supernatant 2 |
| Comparative group 3 | Single-LAB fermented culture supernatant 3 |
| Comparative group 4 | Single-LAB fermented culture supernatant 4 |
| Experimental group 1 | Four-LAB fermented culture supernatant 1 |
| Experimental group 2 | Four-LAB fermented culture supernatant 2 |
| Experimental group 3 | Four-LAB fermented culture supernatant 3 |
| Experimental group 4 | Four-LAB fermented culture supernatant 4 |
| Experimental group 5 | Four-LAB fermented culture supernatant 5 |

Thereafter, 0.02 mL of the liquid culture of *Lactobacillus rhamnosus* MP108 of each group, and the growth medium of the blank control group were subjected to light absorbance measurement at a wavelength of 600 nm ($OD_{600}$) using uQuant™ microplate spectrophotometer (Manufacturer: BioTek Instruments).

The relative growth of *Lactobacillus rhamnosus* MP108 in a respective one of the control group, comparative groups 1 to 4, and experimental groups 1 to 5 was calculated by substituting the thus obtained light absorbance value into the following formula:

$$A=(B-D)/(C-D) \quad (1)$$

where A=relative growth (multiple of control group)

B=$OD_{600}$ of a respective one of control group, comparative groups 1 to 4, and experimental groups 1 to 5

C=$OD_{600}$ of control group

D=$OD_{600}$ of blank control group

The data thus obtained were analyzed according to the procedures as described in section 2 of the General Procedures.

Figure 1:
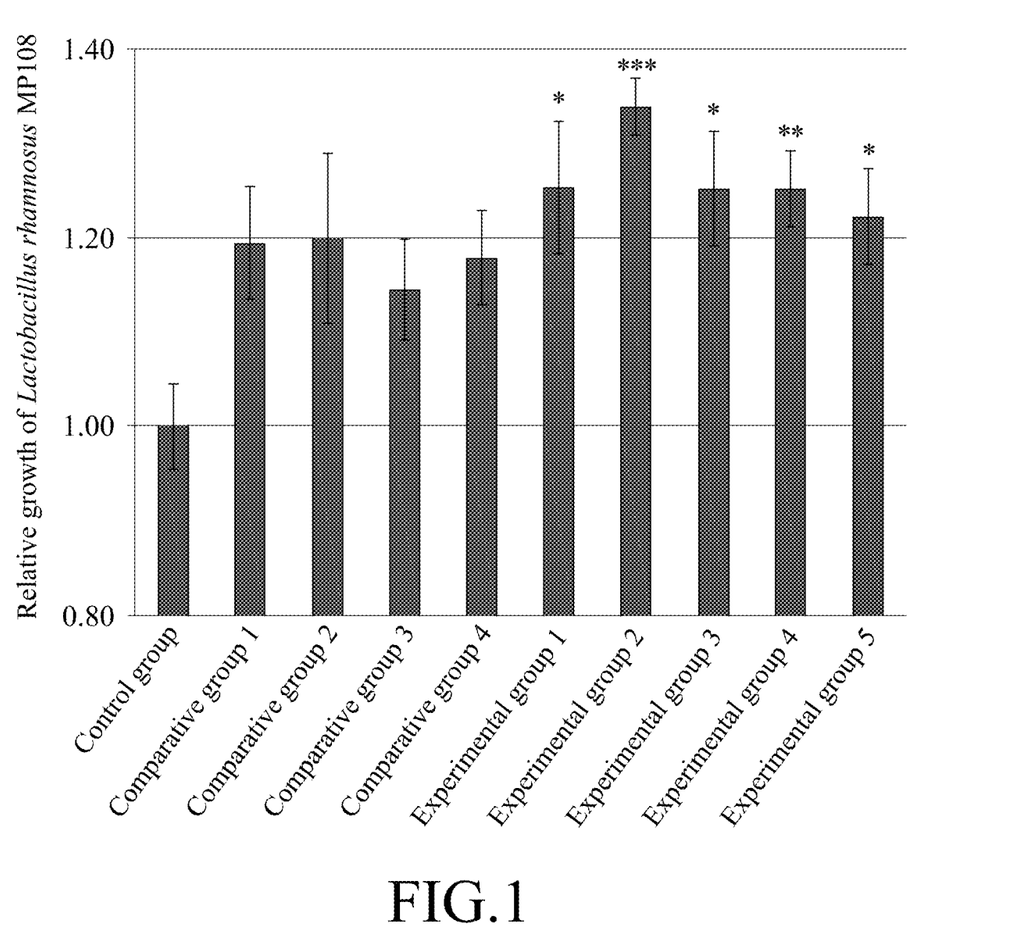
FIG. 1 shows the relative growth of *Lactobacillus rhamnosus* MP108 in each group of Example 2, infra, in which the symbols "*", "" and "*" respectively represent $p<0.05$, $p<0.01$, and $p<0.001$ (compared with the control group)

Results:

FIG. 1 shows the relative growth of *Lactobacillus rhamnosus* MP108 determined in each group. As shown in FIG. 1, the relative growth of *Lactobacillus rhamnosus* MP108 determined in the comparative groups 1 to 4 showed no significant difference compared with that in the control group, while the relative growth of *Lactobacillus rhamnosus* MP108 determined in the experimental groups 1 to 5 was significantly higher than that in the control group. In addition, the relative growth of *Lactobacillus rhamnosus* MP108 determined in the experimental group 2 was higher than those determined in the experimental groups 1, 3, 4 and 5. These results suggest that, *Lactobacillus salivarius* subsp. *salicinius* AP-32, *Lactobacillus plantarum* LPL28, *Lactobacillus acidophilus* TYCA06, and *Bifidobacterium longum* subsp. *infantis* BLI-02, when mixed in a specific number ratio ranging from 1:0.2:0.2:0.2 to 1:5:5:5 and then cultivated to obtain a four-LAB fermented culture supernatant, are capable of producing a synergistic effect to promote the growth of *Lactobacillus rhamnosus* MP108.

Example 3. Evaluation of the Effect of LAB Fermented Culture Supernatant on Promotion of Growth of Various Probiotic Strains In order to evaluate the efficacy of the LAB fermented culture supernatant according to the present disclosure on growth promotion of various probiotic strains, the following experiments were conducted.

Experimental Procedures:

First, the bacterial culture of the respective probiotic strain (see Table 3) obtained in section 1 of the General Procedures was divided into 2 groups, namely, a control group and an experimental group, each having a volume of 5 μL. Thereafter, the experimental group was inoculated into the growth medium containing the four-LAB fermented culture supernatant 2 prepared in Example 1, while the control group was inoculated into a growth medium not containing the four-LAB fermented culture supernatant 2. Next, each group was subjected to cultivation at 37° C. for 6 hours, thereby obtaining a liquid culture of probiotic strain. Subsequently, the liquid culture of the probiotic strain of each group was subjected to light absorbance measurement, followed by determination of relative growth thereof using the procedures described in Example 2. The data thus obtained were analyzed according to section 2 of the General Procedures, and the results were shown in Table 7.

Results:

TABLE 7

| Probiotic strain | Relative growth (multiple of corresponding control group) |
|---|---|
| *Lactobacillus gasseri* AI-88 | 1.62 + 0.11*** |
| *Lactobacillus gasseri* LG21 | 1.15 ± 0.01** |
| *Lactobacillus fermentum* CECT5716 | 1.46 ± 0.05*** |
| *Lactobacillus johnsonii* MH-68 | 1.31 ± 0.07** |
| *Lactobacillus reuteri* GL-104 | 1.39 ± 0.02*** |
| *Lactobacillus helveticus* RE-78 | 1.42 ± 0.09** |
| *Lactobacillus paracasei* MP137 | 1.17 ± 0.05** |
| *Lactobacillus paracasei* ET-66 | 1.27 ± 0.04*** |
| *Lactobacillus rhamnosus* CT-53 | 1.28 ± 0.11** |
| *Lactobacillus rhamnosus* MP108 | 1.34 ± 0.03*** |
| *Lactobacillus rhamnosus* LGG | 1.15 ± 0.03* |
| *Lactobacillus plantarum* LPL28 | 1.26 ± 0.05** |
| *Lactobacillus plantarum* TSP05 | 1.21 ± 0.25* |
| *Lactobacillus acidophilus* TYCA06 | 1.64 ± 0.04** |
| *Lactobacillus acidophilus* LA-5 | 1.77 ± 0.01** |
| *Lactococcus lactis* subsp. *lactis* LY-66 | 1.16 ± 0.04* |
| *Streptococcus thermophilus* SY-66 | 1.33 ± 0.04*** |
| *Streptococcus thermophilus* UASt-09 | 1.20 ± 0.03** |
| *Bifidobacterium animalis* subsp. *lactis* Bb BB-115 | 1.13 ± 0.03** |
| *Bifidobacterium animalis* subsp. *lactis* CP-9 | 1.12 ± 0.03** |
| *Bifidobacterium animalis* subsp. *lactis* BB-12 | 1.27 ± 0.07** |
| *Bifidobacterium longum* subsp. *infantis* BLI-02 | 1.29 ± 0.04** |
| *Bifidobacterium breve* Bv-889 | 1.21 ± 0.04* |
| *Bifidobacterium longum* BB536 | 1.49 ± 0.05*** |

Note:
The symbols "*", "" and "*" respectively represent $p < 0.05$, $p < 0.01$, and $p < 0.001$ as compared to the corresponding control group.

Table 7 shows the relative growth of the probiotic strain determined in each experimental group. As shown in Table 7, the relative growth of the probiotic strain determined in each experimental group was significantly higher compared with that of the corresponding control group. These results suggests that *Lactobacillus salivarius* subsp. *salicinius* AP-32, *Lactobacillus plantarum* LPL28, *Lactobacillus acidophilus* TYCA06, and *Bifidobacterium longum* subsp. *infantis* BLI-02, when mixed in a specific number ratio of 1:1:1:1 and then cultivated to obtain the four-LAB fermented culture supernatant 2, are capable of effectively promoting the growth of probiotic strains of various species.

Example 4. Comparison of the Effect of LAB Fermented Culture Supernatant and Conventional Prebiotics on Promotion of Growth of Probiotic Strains In order to compare the efficacy of the LAB fermented culture supernatant according to the present disclosure with the efficacy of conventional prebiotics on growth promotion of various probiotic strains, the following experiments were conducted.

Experimental Procedures:

First, each of the seven prebiotics described in section 3 of the General Experimental Material and the spray-dried powder of the four-LAB fermented culture supernatant 2 obtained in Example 1 was divided into two portions, which were then dissolved in 4.5 mL of a growth medium as described in section 1 of the General Experimental Material, respectively in an amount of 0.25 wt % and 0.5 wt %, based on the total weight of the growth medium. Therefore, the growth mediums respectively containing the different prebiotics and the four-LAB fermented culture supernatant 2 were obtained. Next, the bacterial culture of *Lactobacillus rhamnosus* MP108 obtained in section 1 of the General Procedures was divided into 18 groups, namely, two control groups (i.e., control groups 1 and 2), fourteen comparative groups (i.e., comparative groups 1-1, 1-2, 2-1, 2-2, 3-1, 3-2, 4-1, 4-2, 5-1, 5-2, 6-1, 6-2, 7-1 and 7-2), and two experimental groups (i.e., experimental groups 1 and 2), each having a volume of 5 μL. Thereafter, as shown in Table 8 below, the bacterial cultures of *Lactobacillus rhamnosus* MP108 of the experimental groups and 2 were respectively inoculated into the aforesaid growth mediums containing the four-LAB fermented culture supernatant 2 at a final concentration of 0.25 wt % or 0.5 wt %, and the bacterial cultures of the comparative groups 1-1, 1-2, 2-1, 2-2, 3-1, 3-2, 4-1, 4-2, 5-1, 5-2, 6-1, 6-2, 7-1 and 7-2 were respectively inoculated into the aforesaid growth mediums containing different prebiotics at a final concentration of 0.25 wt % or 0.5 wt %, while the bacterial cultures of *Lactobacillus rhamnosus* MP108 of the control groups 1 and 2 were respectively inoculated into growth mediums not containing any of the aforesaid four-LAB fermented culture supernatant 2 or the prebiotic. Subsequently, cultivation was conducted at 37° C. for 6 hours, thereby obtaining liquid cultures of *Lactobacillus rhamnosus* MP108.

In addition, in order to determine the efficacy of the four-LAB fermented culture supernatant 2 on the promotion of growth of other probiotic strains or a probiotic mixture, each of the bacterial cultures of *Bifidobacterium animalis* subsp. *lactis* CP-9 and the probiotic mixture including the bacterial cultures of *Lactobacillus rhamnosus* MP108, *Bifidobacterium animalis* subsp. *lactis* Bb BB-115, and *Bifidobacterium longum* subsp. *infantis* BLI-02, as prepared in section 1 of the General Procedures was divided into 18 groups similar to those of the bacterial culture of *Lactobacillus rhamnosus* MP108 (see Table 8), which were then subjected to the aforesaid experimental procedures described for *Lactobacillus rhamnosus* MP108, so as to obtain liquid cultures of *Bifidobacterium animalis* subsp. *lactis* CP-9 and the probiotic mixture.

TABLE 8

| Group | Final concentration (wt %) | Prebiotic or four-LAB fermented culture supernatant 2 |
|---|---|---|
| Control group 1 | 0 | — |
| Control group 2 | 0 | — |
| Comparative group 1-1 | 0.25 | Human milk oligosaccharides |
| Comparative group 1-2 | 0.5 | |
| Comparative group 2-1 | 0.25 | Maltodextrin |
| Comparative group 2-1 | 0.5 | |
| Comparative group 3-1 | 0.25 | Fructooligosaccharides |
| Comparative group 3-2 | 0.5 | |
| Comparative group 4-1 | 0.25 | Galactooligosaccharides |
| Comparative group 4-2 | 0.5 | |
| Comparative group 5-1 | 0.25 | Sorbitol |
| Comparative group 5-2 | 0.5 | |
| Comparative group 6-1 | 0.25 | Erythritol |
| Comparative group 6-2 | 0.5 | |
| Comparative group 7-1 | 0.25 | Inulin |

TABLE 8-continued

| Group | Final concentration (wt %) | Prebiotic or four-LAB fermented culture supernatant 2 |
|---|---|---|
| Comparative group 7-2 | 0.5 | |
| Experimental group 1 | 0.25 | Four-LAB fermented culture supernatant 2 |
| Experimental group 2 | 0.5 | |

Subsequently, the liquid cultures of *Lactobacillus rhamnosus* MP108, *Bifidobacterium animalis* subsp. *lactis* CP-9, and the probiotic mixture were subjected to light absorbance measurement, followed by determination of relative growth thereof using the procedures described in Example 2. The data thus obtained were analyzed according to section 2 of the General Procedures, and the results are shown in FIGS. 2 to 4.

Figure 2:
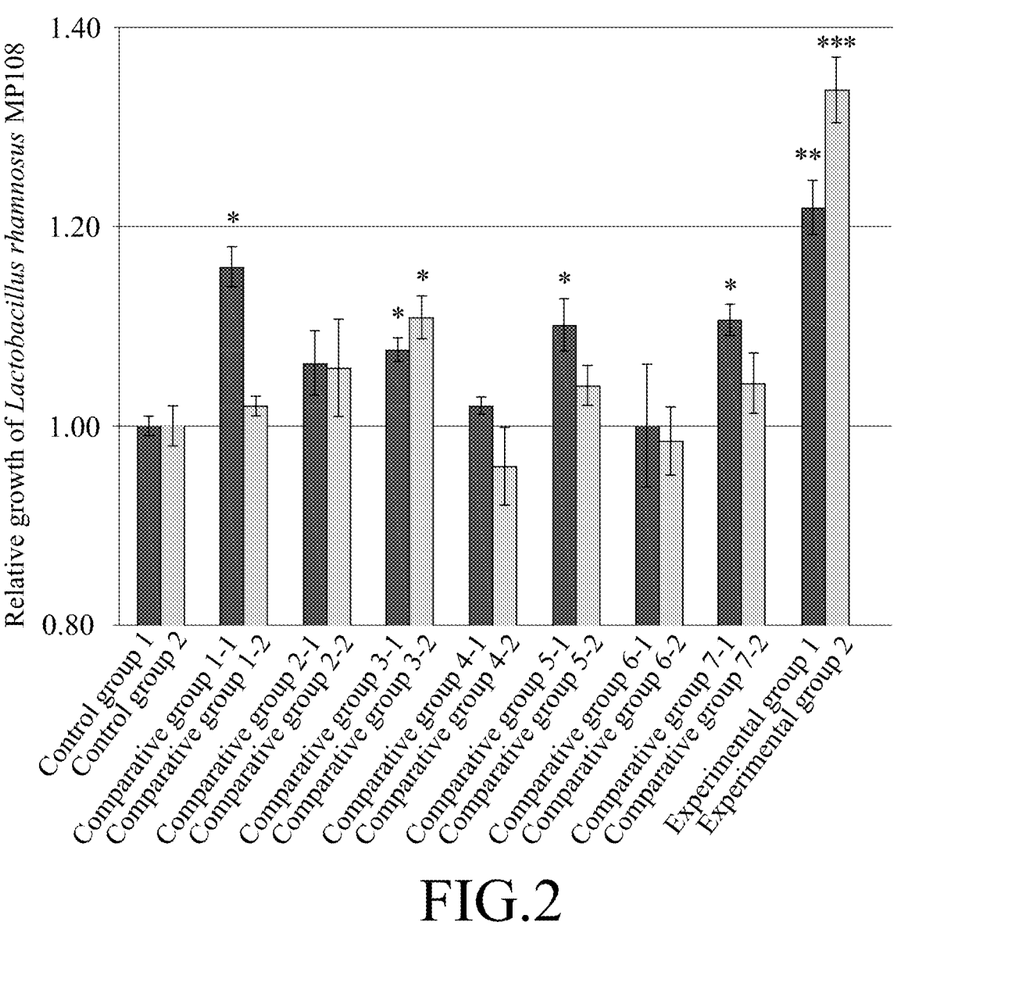
FIG. 2 shows the relative growth of *Lactobacillus rhamnosus* MP108 in each group of Example 4, infra, in which the symbols "*", "*" and "***" respectively represent $p<0.05$, $p<0.01$, and $p<0.001$ (compared with the corresponding control group)
Figure 3:
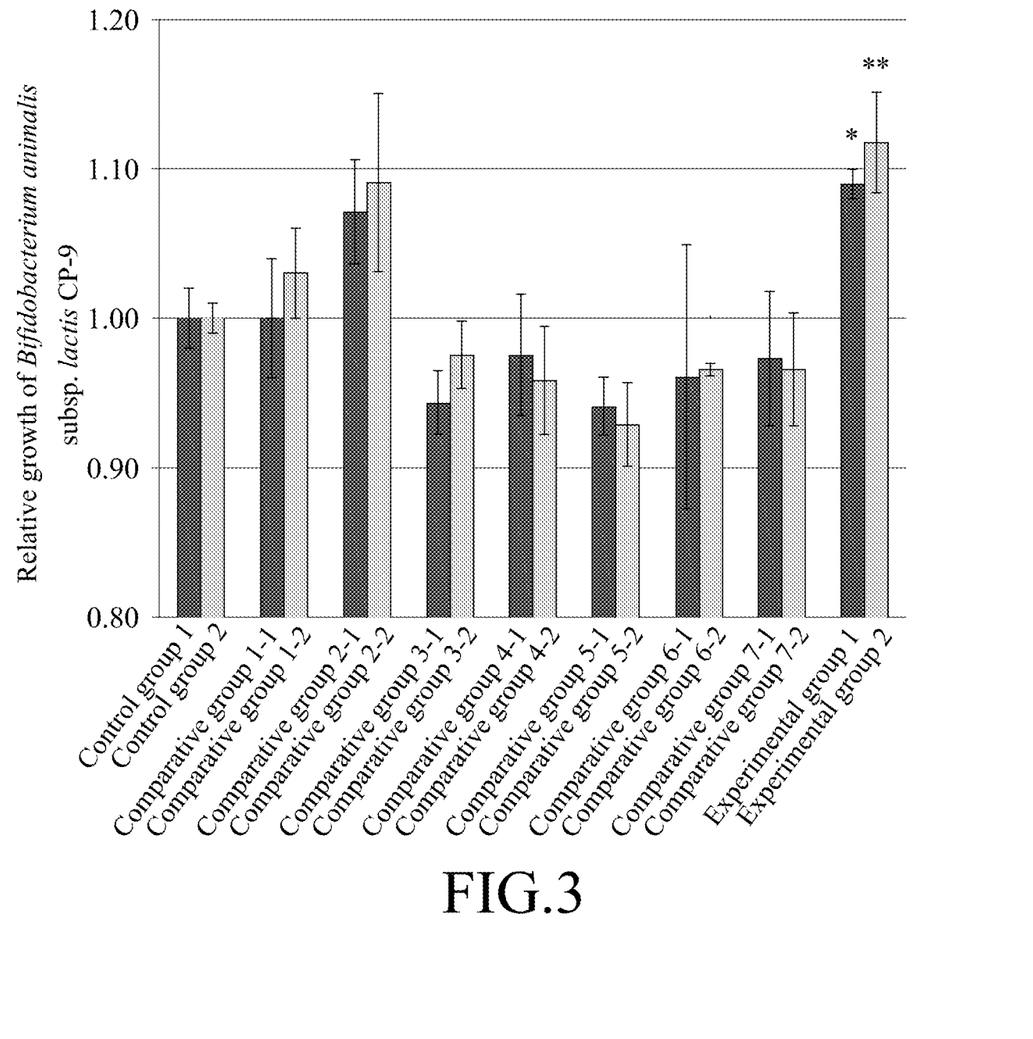
FIG. 3 shows the relative growth of *Bifidobacterium animalis* subsp. *lactis* CP-9 in each group of Example 4, infra, in which the symbols "*" and "**" respectively represent $p<0.05$ and $p<0.01$ (compared with the corresponding control group)
Figure 4:
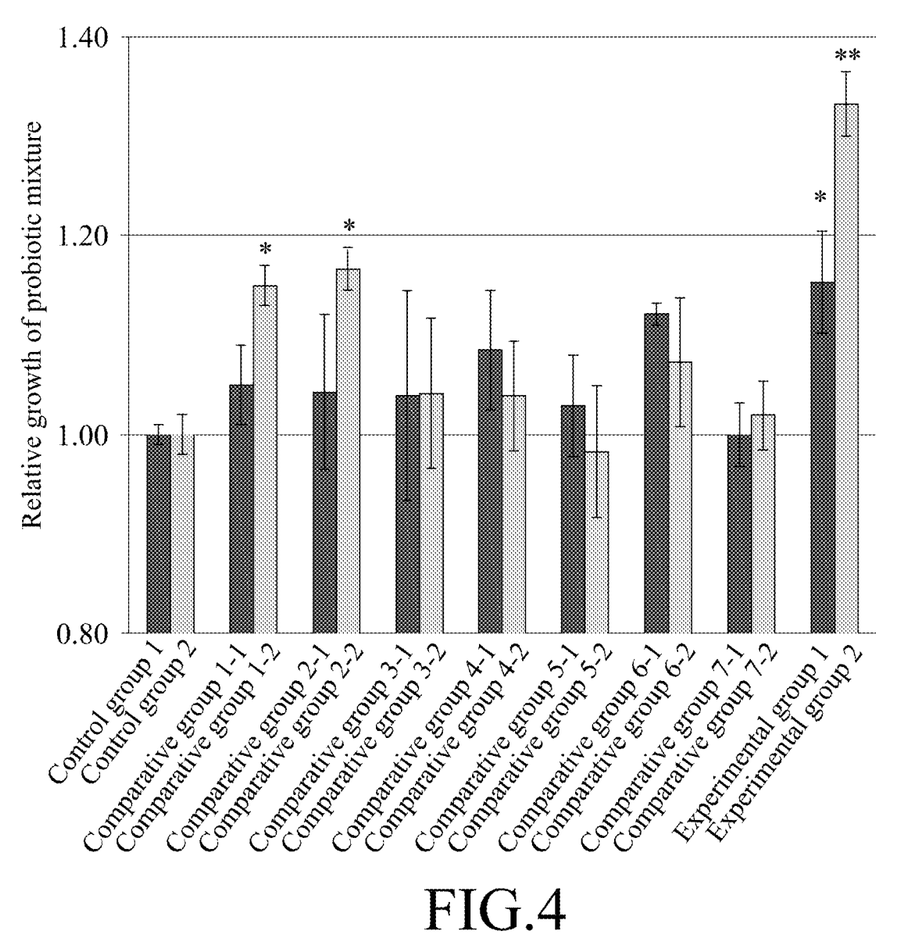
FIG. 4 shows the relative growth of a probiotic mixture including *Lactobacillus rhamnosus* MP108, *Bifidobacterium animalis* subsp. *lactis* Bb BB-115, and *Bifidobacterium longum* subsp. *infantis* BLI-02 in each group of Example 4, infra, in which the symbols "*" and "**" respectively represent $p<0.05$ and $p<0.01$ (compared with the corresponding control group).

Results:

FIGS. 2 to 4 respectively show the relative growth of *Lactobacillus rhamnosus* MP108, *Bifidobacterium animalis* subsp. *lactis* CP-9, and the probiotic mixture including *Lactobacillus rhamnosus* MP108, *Bifidobacterium animalis* subsp. *lactis* Bb BB-115 and *Bifidobacterium longum* subsp. *infantis* BLI-02 determined in each group (the relative growth is expressed as multiple of corresponding control group). As shown in FIGS. 2 to 4, each of the conventional prebiotics was not necessarily able to effectively promote the growth of *Lactobacillus rhamnosus* MP108, *Bifidobacterium animalis* subsp. *lactis* CP-9, and the probiotic mixture. In contrast, the four-LAB fermented culture supernatant 2, which was prepared by mixing the LAB inoculums of *Lactobacillus salivarius* subsp. *salicinius* AP-32, *Lactobacillus plantarum* LPL28, *Lactobacillus acidophilus* TYCA06 and *Bifidobacterium longum* subsp. *infantis* BLI-02 in a specific number ratio of 1:1:1:1 followed by cultivation thereof, was capable of greatly promoting the growth of *Lactobacillus rhamnosus* MP108, *Bifidobacterium animalis* subsp. *lactis* CP-9, and the probiotic mixture. These results indicate that the fermented culture supernatant, which is obtained by mixing *Lactobacillus salivarius* subsp. *salicinius* AP-32, *Lactobacillus plantarum* LPL28, *Lactobacillus acidophilus* TYCA06 and *Bifidobacterium longum* subsp. *infantis* BLI-02 at different concentrations thereof, is capable of promoting the growth of one or more probiotic strains, and hence, can be used to replace conventional prebiotics so as to promote the growth of various types of probiotic microorganisms.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for promoting growth of a probiotic microorganism, comprising cultivating the probiotic microorganism in a growth medium containing a fermented culture of lactic acid bacterial strains, wherein the lactic acid bacterial strains include *Lactobacillus salivarius* subsp. *salicinius* AP-32 which is deposited at the China Center for Type Culture Collection (CCTCC) under an accession number CCTCC M 2011127, *Lactobacillus plantarum* LPL28 which is deposited at the China General Microbiological Culture Collection Center (CGMCC) under an accession number CGMCC 17954, *Lactobacillus acidophilus* TYCA06 which is deposited at the CGMCC under an accession number CGMCC 15210, and *Bifidobacterium longum* subsp. *infantis* BLI-02 which is deposited at the CGMCC under an accession number CGMCC 15212,
wherein the probiotic microorganism includes *Lactococcus lactis* or *Streptococcus thermophilus*.

2. The method as claimed in claim 1, wherein the fermented culture is obtained by cultivating *Lactobacillus salivarius* subsp. *salicinius* AP-32, *Lactobacillus plantarum* LPL28, *Lactobacillus acidophilus* TYCA06, and *Bifidobacterium longum* subsp. *infantis* BLI-02 in a ratio of colony forming units ranging from 1:0.2:0.2:0.2 to 1:5:5:5 in a liquid medium suitable for growth thereof.

3. The method as claimed in claim 2, wherein the ratio of colony forming units of *Lactobacillus salivarius* subsp. *salicinius* AP-32, to *Lactobacillus plantarum* LPL28, to *Lactobacillus acidophilus* TYCA06, and to *Bifidobacterium longum* subsp. *infantis* BLI-02 is 1:1:1:1.

4. The method as claimed in claim 1, wherein the probiotic microorganism further includes *Lactobacillus* spp. which is selected from the group consisting of *Lactobacillus gasseri, Lactobacillus fermentum, Lactobacillus johnsonii, Lactobacillus reuteri, Lactobacillus helveticus, Lactobacillus casei, Lactobacillus paracasei, Lactobacillus rhamnosus, Lactobacillus delbrueckii, Lactobacillus bulgaricus, Lactobacillus salivarius, Lactobacillus plantarum, Lactobacillus acidophilus,* and combinations thereof.

5. The method as claimed in claim 1, wherein the probiotic microorganism further includes *Bifidobacterium* spp. which is selected from the group consisting of *Bifidobacterium animalis, Bifidobacterium breve, Bifidobacterium longum, Bifidobacterium bifidum, Bifidobacterium adolescentis, Bifidobacterium infantis,* and combinations thereof.

* * * * *